(12) United States Patent
O'Connor et al.

(10) Patent No.: US 7,776,346 B2
(45) Date of Patent: *Aug. 17, 2010

(54) PERSONAL PRODUCT COMPOSITIONS COMPRISING STRUCTURED BENEFIT AGENT PREMIX OR DELIVERY VEHICLE

(75) Inventors: Stephen M. O'Connor, New York, NY (US); Michael Joseph Fair, Ridgewood, NJ (US); John Richard Nicholson, Ramsey, NJ (US); Bozena Marianna Piatek, Cedar Grove, NJ (US); David John Lang, Ossining, NY (US); Gregory McFann, North Bergen, NJ (US); Birnur Aral, West New York, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 393 days.

This patent is subject to a terminal disclaimer.

(21) Appl. No.: 10/443,393

(22) Filed: May 22, 2003

(65) Prior Publication Data

US 2004/0234558 A1    Nov. 25, 2004

(51) Int. Cl.
  A61K 8/02    (2006.01)
  A61K 45/00   (2006.01)

(52) U.S. Cl. .................................................... 424/401

(58) Field of Classification Search ................ 424/400, 424/401, 70.8, 70.19–70.31, 74; 510/130, 510/141, 159
See application file for complete search history.

(56) References Cited

U.S. PATENT DOCUMENTS

| | | | |
|---|---|---|---|
| 3,211,619 A | | 10/1965 | Buchwelter et al. |
| 5,154,849 A * | | 10/1992 | Visscher et al. ............. 510/150 |
| 5,437,859 A | | 8/1995 | Ser et al. |
| 5,661,189 A | | 8/1997 | Grieveson et al. |
| 5,674,511 A | | 10/1997 | Kacher et al. |
| 5,804,540 A | | 9/1998 | Tsaur et al. |
| 5,817,609 A | | 10/1998 | He et al. |
| 5,935,917 A * | | 8/1999 | Farrell et al. ................ 510/141 |
| 5,981,464 A * | | 11/1999 | He et al. ..................... 510/451 |
| 6,057,275 A * | | 5/2000 | Fair et al. .................... 510/151 |
| 6,066,608 A | | 5/2000 | Glenn, Jr. et al. |
| 6,080,707 A | | 6/2000 | Glenn, Jr. et al. |
| 6,080,708 A | | 6/2000 | Glenn, Jr. et al. |
| 6,174,845 B1 * | | 1/2001 | Rattinger et al. ............ 510/146 |
| 6,338,840 B1 | | 1/2002 | Allan et al. |
| 6,413,922 B1 * | | 7/2002 | Goo et al. .................... 510/156 |
| 6,458,751 B1 * | | 10/2002 | Abbas et al. ................ 510/141 |
| 6,491,935 B1 | | 12/2002 | Bekele |
| 6,534,457 B2 * | | 3/2003 | Mitra ......................... 510/130 |
| 6,645,511 B2 * | | 11/2003 | Aronson et al. ............. 424/401 |
| 6,669,763 B1 | | 12/2003 | Ghodoussi |
| 6,673,755 B2 | | 1/2004 | Wei et al. |
| 6,716,440 B2 * | | 4/2004 | Aronson et al. ............. 424/401 |
| 2003/0049282 A1 | | 3/2003 | Aronson et al. |
| 2003/0054019 A1 | | 3/2003 | Aronson et al. |
| 2003/0082222 A1 * | | 5/2003 | Miyamoto ................... 424/401 |
| 2003/0083210 A1 | | 5/2003 | Goldberg et al. |

FOREIGN PATENT DOCUMENTS

| | | |
|---|---|---|
| EP | 0 294 893 | 12/1988 |
| EP | 413 417 | 2/1995 |
| EP | 1 486 195 | 12/2004 |
| GB | 2235930 A | 3/1991 |
| WO | 02/39974 | 5/2002 |
| WO | 02/096373 A2 | 12/2002 |
| WO | 03/074020 A1 | 9/2003 |
| WO | 03/082222 | 10/2003 |

OTHER PUBLICATIONS

Co-pending application for Kerschner et al.; U.S. Appl. No. 10/443,394, filed May 22, 2003 for Personal Product Compositions Comprising Structured Benefit Agent Premix or Delivery Vehicle and Providing Enhanced Effort of Hydrophobic Material Separate from the Structured Benefit Agent.
Co-pending application for Zhang et al.; U.S. Appl. No. 10/443,396, filed May 22, 2003 for Personal Product Compositions Comprising Structured Benefit Agent Premix or Delivery Vehicle and Providing Enhanced Effort of Optical Modifier Separate from Structured Benefit Agent.
Co-pending application for Ananthapadmanabhan et al.; U.S. Appl. No. 10/443,392, filed May 22, 2003 for Personal Product Compositions Comprising Structured Benefit Agent Premix or Delivery Vehicle and Proving Enhanced Effort of Hydrophilic Benefit Agent.
Co-pending application for Pham et al.; U.S. Appl. No. 10/443,569, filed May 22, 2003 for Non-bar Personal Product Compositions Comprising Crystalline Wax Structured Benefit Agent Premix or Delivery Vehicle.
Communication Under Rule 71(3) EPC on Application No. 04 252 715.0-2108 dated Mar. 12, 2008.

* cited by examiner

*Primary Examiner*—Sreeni Padmanabhan
*Assistant Examiner*—Layla Soroush
(74) *Attorney, Agent, or Firm*—Ronald A. Koatz

(57) ABSTRACT

The present invention relates to compositions comprising a structured benefit agent pre-mix or delivery vehicle comprising benefit agent structured with crystalline materials, as defined, which when separately prepared and combined after preparation, provides enhanced delivery of benefit agent to a carrying composition into which the premix is added.

6 Claims, 4 Drawing Sheets

PERSONAL PRODUCT COMPOSITIONS COMPRISING STRUCTURED BENEFIT AGENT PREMIX OR DELIVERY VEHICLE

FIELD OF THE INVENTION

The present invention comprises a structured premix or "delivery vehicle" composition designed to enhance delivery (e.g., via enhanced deposition) of hydrophobic benefit agent(s), for example, moisturizing oils, from personal product compositions (e.g., bars, liquid soap, creams, emulsions, non-wovens, etc.). When the structured benefit agent composition is separately prepared and combined with the personal product composition, a personal product carrying composition is provided which yields enhanced delivery of the benefit agent(s).

It should be noted that not only the benefit agent which is structured will benefit from enhanced delivery, but also benefit agents which are separately found in the composition (e.g., entrapped within a network formed by the structured benefit agent or added separately and not as part of the premix) also may have enhanced delivery. The separate, not necessarily independently structured benefit agent (and certainly not structured as delivered in the invention if not added with the premix) may be other hydrophobic benefit agents (e.g., perfumes, shine enhancing benefit agents, emollients) or hydrophilic benefit agents (e.g., glycerol).

BACKGROUND

Hydrophobic benefit agents (e.g., oils) can provide moisturizing and/or conditioning benefits to the skin or hair. At present, however, it is extremely difficult to achieve high levels of deposition from personal product compositions, particularly wash-off products, such as personal wash liquid and bar cleansers.

While this and co-pending applications are described with skin cleansing personal product language, to the extent the structured benefit agents can be used in a variety of other compositions where deposition of benefit agents is desirable (e.g., hair, deodorant), the claims are intended to be read expansively and limited only by the structuring component.

Unexpectedly, applicants have found that use of certain "structured" benefit agents (e.g., oils and other hydrophobic benefit agents) act as so-called delivery vehicles for the benefit agent(s) leading to multiple benefits relative to benefit agents which are delivered without the specific structuring of the invention; or relative to other benefit agents used in the final composition where no other structured benefit agents are used. According to the invention, preferably the benefit agent being structured and the structuring material (e.g., hydrogenated oil or fat) are separate components.

By specifically selecting particular crystalline structurant or structurants (i.e., so that the crystals have specifically defined aspect ratios), and by separately preparing structured benefit agent as a premix in the manner described (i.e., separate preparation and incorporation into product in molten, semi-molten or solid state), the benefit agent structurant vehicle (i.e., structured benefit agent vehicle) provides enhanced deposition as well as desired in-use and after-use sensory attributes (e.g., smooth skin feel).

As noted, such structured benefit agent also helps deposition of other benefit agents whether used in the same pre-mix (it is not clear whether they are separately structured or trapped in a network, but result is same), or whether separately added with other composition components.

Specifically, the invention relates to the use of hydrophobic benefit agent or agents structured by crystalline structurant or structurants selected from the group consisting of crystalline structuring materials (e.g. fats or hydrogenated oils) wherein, when the structured benefit vehicle is separately prepared before combining with the personal product composition, for example, the final composition is provided with enhanced benefit agent deposition to substrate. This enhanced deposition is dependent on the benefit agent, but can broadly be defined as at least 5% greater, preferably at least 10% greater and often far more than the level of deposition obtained if the benefit agent was added without being structured or without being in the presence of a structured benefit agent in the final formulation.

In one embodiment, benefit agents (i.e., benefit agent oils) are deposited from a personal product liquid cleanser composition, in an amount of greater than about 60 $\mu$g/cm$^2$ (measured in accordance with protocol for measuring deposition from liquids described herein). In a second embodiment, benefit agents (i.e., benefit agent oils) deposited from a personal product bar composition, for example, provide the final composition with benefit agent deposition greater than about 5 $\mu$g/cm$^2$ (according to protocol for measuring deposition from bars). Unlike prior art references where deposition is dependent on the large size of the benefit agent droplets (e.g., >50 micrometers average droplet diameter), the deposition results of the subject invention have no requirement of large droplet size. The structured benefit agent also provides enhanced deposition of hydrophobic or hydrophilic benefit agents separately added.

Among the crystalline materials which may be used are included hydrogenated oils or fats, fatty acids, fatty alcohols, salts of fatty acids, hydroxy fatty acids and fatty acid esters.

Some prior art references purport to use rheological parameters to select oils or oil blends to be used for improving deposition or providing favorable sensory feel. U.S. Pat. No. 5,674,511 to Kacher et al., for example, describes the use of solubility parameters and four rheological parameters to select benefit agents (i.e., oil or oil blends) that can be used in moisturizing cleansing formulations to improve deposition and provide favorable sensory feels. Petrolatum and petrolatum-containing mixtures are said to be favorable selections. The reference fails to teach or suggest the building of a deformable network of crystals within the benefit agent for which crystals must have a specific aspect ratio. The Kacher reference fails to teach or suggest that the structured benefit agent can be combined with other components in the compositions in a molten, semi-molten or solid state. Also, it does not describe separate benefit agent and structurant, as is preferred by the subject invention (i.e., in the subject invention, if petrolatum is used, it is used as a structurant to structure other benefit agents rather than itself comprise the structured benefit agent). In short, the benefit agents (e.g., oils) of Kacher clearly do not appear to be internally structured delivery vehicles like those used in the compositions of the invention which are separately prepared and wherein structurant has a defined aspect ratio.

A number of prior art references disclose generally the concept of an oil additive which can thicken or stabilize oils. They do not, however teach or disclose that specific crystalline structurant (i.e., having a defined aspect ratio), when prepared in combination with a hydrophobic benefit agent as a premix/delivery vehicle (added in a molten, semi-molten or solid state; and combined with a carrying composition), will enhance deposition (e.g., in an amount at least 5% greater than if no structured benefit agent is used at all and/or will provide enhanced sensory benefits). Moreover, in contrast to these references where deposition is disclosed as a function of large droplet size of the benefit agent, in the subject invention deposition will occur independent of such large droplet size requirement.

U.S. Pat. No. 5,804,540 to Tsaur et al. and U.S. Pat. No. 5,661,189 to Grieveson, for example, disclose use of both crystalline or micro-crystalline waxes and hydrophobic polymers to thicken low viscosity oil so as to control the oil droplet size (i.e., it must attain a certain minimum size to deposit) as well as to maintain high lather. As noted above, however, there is no discussion of the criticality of crystalline structure (aspect ratio) or that a thickened benefit agent must be separately prepared and added in a molten, semi-molten or solid state. Further, as noted, there is no recognition that it is critical the thickener must be a natural or synthetic crystalline structuring material (as is the case with subject invention) or that deposition occurs without the need for large droplet size. Indeed, the preferred thickening materials claimed in these patents provide only a very modest enhancement of deposition of low viscosity oils when they are incorporated into the subject invention.

In co-pending U.S. patent application Ser. No. 09/859,862 to Aronson et al. (entitled "Wet-Skin Treatment Composition"), filed May 17, 2001 and 09/859,849 to Aronson et al. (entitled "Method of Enhanced Moisture or Reduced Drying Using Wet-Skin Treatment Compositions"), there is disclosed benefit agents which provide a draggy feel. There is no teaching or disclosure however, of using benefit agent structurant with crystalline materials of specific aspect ratio or of how to produce such.

There is also some bar art relating to mixing benefit agents and carriers for use in soap base. U.S. Pat. No. 6,242,398 to Chambers et al., for example, discloses soap bar prepared by premixing benefit agents such as oils and humectants with solid carriers such as starches, followed by mixing with soap bar.

No prior art of which applicants are aware demonstrates the use of hydrogenated oils, fats, fatty acids or fatty alcohols having specific aspect ratio of crystals and prepared as a premix to enhance the deposition of benefit agents (e.g., skin nutrients such as, for example, sunflower seed oil).

Additionally, there is no prior art of which applicants are aware that demonstrates the use of these materials for structuring hydrophobic benefit agents so as to improve the properties (e.g., hardness, wear rate, mush) of personal product bars containing such benefit agents.

BRIEF DESCRIPTION OF THE INVENTION

Accordingly, the present invention relates to both bar and non-bar personal wash or personal product compositions (including bars, liquid soap, creams, emulsions, non-wovens, deodorant compositions, hair composition or any other compositions where enhanced benefit agent delivery is described), preferably compositions comprising structured benefit agent composition for delivering a benefit agent(s) (e.g., oil).

Liquid compositions of the invention comprise:

(1) 0-99%, preferably 1 to 75%, more preferably 3 to 70% by wt. surfactant; and (2) 0.1 to 90% by wt. of a benefit agent delivery vehicle (structured benefit agent) wherein:

(a) 0.1 to 99.9, preferably 0.5 to 99.5, more preferably 1 to 99% by wt. of the structured delivery vehicle comprises one or more benefit agents or mixtures thereof; and (b) 99.9 to 0.1%, preferably 99.5 to 0.5% by wt. of the structured delivery vehicle comprise a crystalline structurant or structurants selected from the group consisting of hydrogenated oils, fats, fatty acids, and fatty alcohols;

wherein crystals of the crystalline structurant have an aspect or axial ratio such that length A to width B of the crystals has a ratio A/B>1. The length is to be understood as the longer of the two dimensions when considering both length and width.

Bar compositions of the invention comprise:

(1) 1 to 80%, preferably 3 to 65% by wt. surfactant; and (2) 0.1 to 90% by wt. of a benefit agent delivery vehicle (structured benefit agent) wherein:

(a) 0.1 to 99%, preferably 0.5 to 99.5, more preferably 1 to 99% by wt. of the structured delivery vehicle comprising one or more benefit agents or mixtures thereof; and (b) 99.9 to 0.1%, preferably 99.5 to 0.5% by wt. of the structured delivery vehicle comprises a crystalline structurant or structurants selected from the group consisting of hydrogenated oils, fats, fatty acids and fatty alcohols;

wherein crystals of the crystalline structurant (e.g. wax) have an aspect or axial ratio such that length A to width B of the crystals has a ratio A/B>1. The length is to be understood as the longer of the two dimensions when considering both length and width.

When a premix (structured benefit agent composition) is separately prepared and properly combined with a carrying composition (e.g., surfactant containing or non-surfactant containing personal product composition) in which the structured benefit agent will be used to deliver the benefit agent to the substrate, said composition will have benefit agent deposition from the composition of at least 5% greater, preferably at least 10% greater relative to level of deposition from the final composition if the same benefit agent had not been structured in accordance to the invention, or if the benefit agent had not been in the presence of a structured benefit agent in the final formulation.

In one embodiment of the invention, the composition is a liquid composition and said liquid composition will have benefit agent deposition (e.g., oil deposition) of greater than about 60 $\mu g/cm^2$. In another embodiment, the composition is a bar composition and said bar composition will have benefit agent deposition (e.g., oil) greater than about 5 $\mu g/cm^2$. For incorporation into products, the structured benefit agent premix can be in molten, semi-molten or solid state. The deposition of the benefit agent is not dependent on large droplet size (i.e., can be small or large drops).

The use of structured benefit agent also enhances delivery of benefit agent(s) in the premix which may not be independently structured (e.g., may be caught in a network) or which may be added separately and not as part of the premix.

The structured benefit agent or delivery vehicle of this invention may be used in personal product skin cleansing compositions. It may also be used, for example, in hair and deodorant compositions.

In another aspect of the invention, the invention comprises a process for forming non-bar, preferably liquid, personal product composition comprising the delivery vehicle noted above which process comprises:

(1) mixing hydrophobic benefit agent or agents and crystalline structurant at processing conditions (e.g., a temperature sufficiently high) so that a premix of the benefit agent and structurant and preferably will be flowable and will pour (e.g., having viscosity of less than 250 Pa-s, more preferably less than 200 Pa-s, most preferably less than 100 Pa-s);

(2) combining said separately prepared premix and the carrying composition, preferably with stirring;

(3) if necessary, because the mixture had been heated, cooling the resulting mixture to room temperature.

In another aspect of the invention, the invention comprises a process for forming a personal cleansing bar product composition comprising the delivery vehicle noted above which process comprises:

(1) mixing hydrophobic benefit agent or agents and crystalline structurant at a temperature above the melting point of the structurant and then either cooling to ambient temperature so that it can be combined later with the bar carrying composition, or optionally cooling to the temperature at which the carrying composition is mixed before combining with the carrying composition;

(2) combining said separately prepared premix and the carrying composition, preferably with stirring or mixing at elevated temperature;

and then either (3) pouring the resulting mixture into molds and cooling (actively or passively) to room temperature; or (4) cooling the resulting mixture to flakes (e.g., by passing the resulting mixture over a chill roll), taking the flakes (e.g., from the chill roll) and extruding the material into a billet which is then formed or stamped.

In another embodiment, the invention provides a method for enhancing deposition of hydrophobic benefit agent and providing smooth skin feel which method comprises applying a personal product cleanser comprising:

(a) 0 to 99% surfactant; and (b) 0.1 to 90% of benefit agent vehicle wherein:

(i) 0.1 to 99.9% by wt. structured benefit agent vehicle comprises one or more benefit agents or mixtures thereof; and (ii) 99.9 to 0.1% by wt. of structured benefit agent vehicle of a crystalline structurant wherein the structurant is selected as noted above.

DETAILED DESCRIPTION OF THE INVENTION

The present invention relates to personal product compositions comprising a structured benefit agent delivery vehicle composition which, because of the structure of the crystal used to prepare it (for example, aspect ratio of the crystalline structurants), and its manner of preparation (separately prepared), forms a structured benefit agent component. The structured benefit agent component has particular properties (e.g., yield stress, shear thinning) that permit the structured benefit agent component to deposit more efficiently from the composition onto skin or other substrate. Further, use of the structured benefit agents permits enhanced deposition of other benefit agents in the premix (whether entrapped or independently added) as well as those in the composition and separately added.

Figure 1:
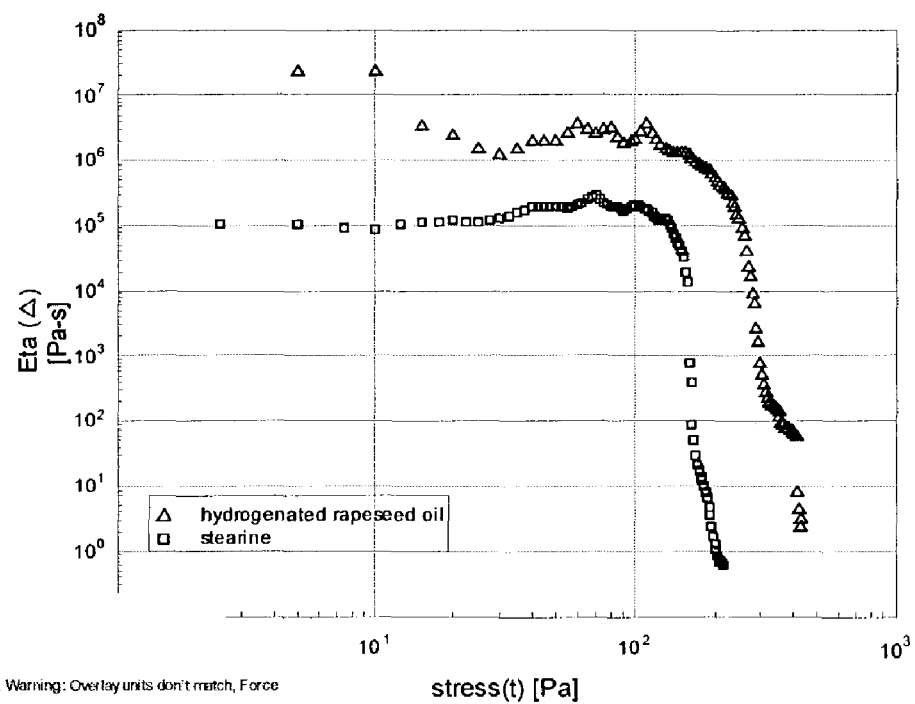
FIG. 1 is a yield stress plot of a structured benefit agent composition comprising sunflower seed oil structured with a crystalline structurant of the invention. Akofine R (hydrogenated rapeseed oil) was mixed with sunflower seed oil at a ratio of 2:3 (hydrogenated rapeseed oil/sunflower seed oil). Stearine 07 (hydrogenated cottonseed oil) was mixed with sunflower seed oil at a ratio of 1:9. The graph shows how the structured benefit agent yields under high stress—a property specific to be structured benefit agents of the invention. At low stresses the viscosity of the structured benefit agent composition, (measured in Pascal seconds, or Pa-s) is essentially constant. As the applied stress is increased and reaches the yield stress value, the viscosity drops sharply and the material flows more readily.
Figure 2:
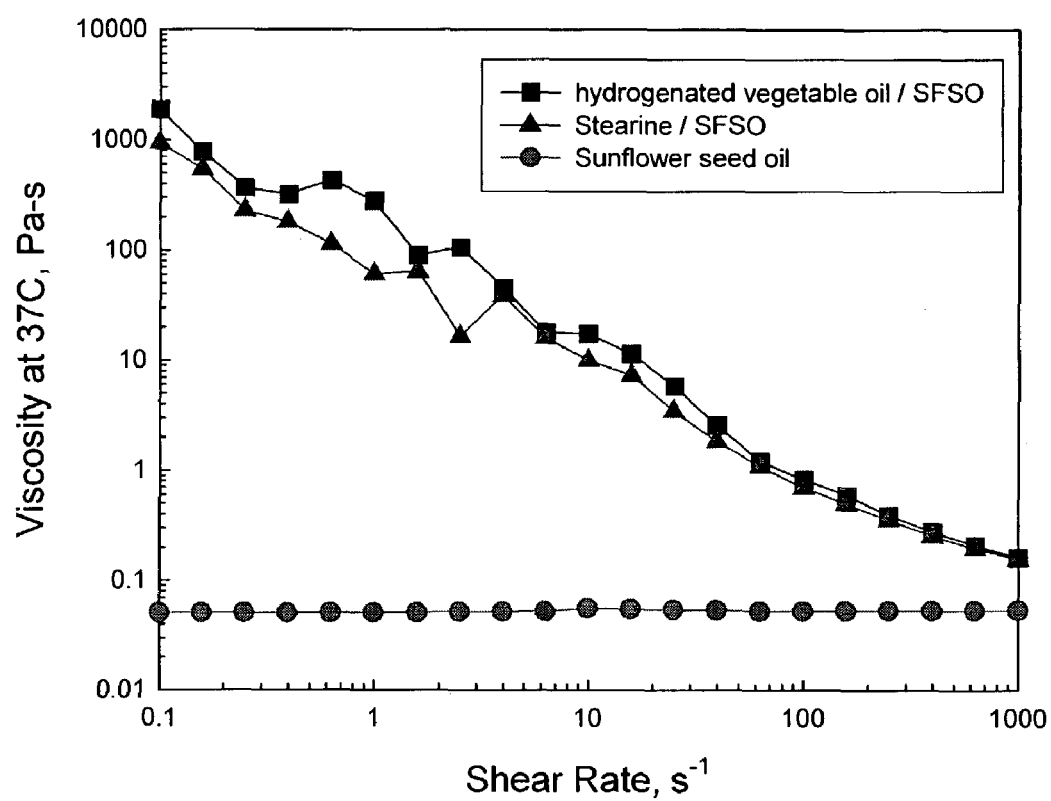
FIG. 2 is a plot showing shear thinning behavior of structured benefit agents of the invention versus an unstructured benefit agent. Lipex 408 (hydrogenated vegetable oil) was mixed with sunflower seed oil at a ratio of 1:4 (Lipex 408 oil/sunflower seed oil). Stearine 07 was mixed with sunflower seed oil at a ratio of 1:9. For comparison, the viscosity behavior with shear of unstructured sunflower seed oil is also shown. Plotted is viscosity versus shear rate. At low shear rates, the viscosity of structured benefit agents, sunflower seed oil structured with Lipex 408 or that structured with Stearine 07 is very high. As the applied shear rate is increased the viscosity of the structured benefit agents decreases and continues to decrease at the higher shear rates. At sufficiently high shear rates the viscosity of structured benefit agents approaches that of the pure unstructured benefit agent component.

Yield stress parameters can be 1-5000 Pa or higher and all ranges subsumed therein (see FIG. 1) and shear thinning parameters can range from 2000 Pa-s (or higher) at low shear rates (0.1/sec) (i.e., viscosity of 1000 to 10,000 Pa-s as seen on the Y axis of FIG. 2) to 0.1 Pa-s (or lower) at high shear rates (100/sec) (again, see FIG. 2). Both yield stress and shear-thinning parameters/ranges are dependent on the level of benefit agent structurant added to benefit agent.

When specific crystalline materials are used to structure the structured benefit agent, and when the process of the invention is used, final composition containing the structured benefit agent vehicle will provide enhanced delivery of the hydrophobic benefit agent to the skin or substrate at an exceedingly efficient level from compositions, e.g., at least 5% improvement, preferably at least 10% improvement relative to if the benefit agent were either not structured or not separately added outside the premix but in the presence of a structured benefit agent in the final formulation. In a liquid embodiment, oils can deposit from the liquid at greater than about 60 µg/cm$^2$, preferably greater than 100 µg/cm$^2$. In a bar embodiment, oils can deposit from a bar at greater than 5 µg/cm$^2$. Moreover, such deposition is not dependent on large droplet size of the structured benefit agent droplets in the carrying composition (e.g., liquid or bar soaps).

The "structured" benefit agent (e.g., oil) of the subject invention can be envisioned as an emollient droplet which has certain physical properties defining at least in part the ability of the structured benefit agent to deliver the benefit agent more efficiently from the final composition.

More specifically, when crystalline materials structure the benefit agent, the crystals in the benefit agent phase are believed to create a solid network which is apparently interconnected like a "house of cards" for plate-like crystals or perhaps more like a scaffold structure when the crystalline structurant has rod/needle morphology. The crystals form a three-dimensional supporting network that, without wishing to be bound by theory, is believed to make the structured benefit agents, for example, more than just thickened benefit agents (see FIG. 4). The crystalline structure changes the normally fluid benefit agent (e.g., vegetable or other oils) into solid-like materials that have good flow and spreading properties for benefit agent deposition. Through selection of structurant (e.g., hydrogenated oil, fat) and calculation of structurant content, the structured benefit agent can be tailored to meet desired rheological parameters. An important part of the invention is that the crystal forming this 3-D network must have an aspect or axial ratio of length and width (A and B, respectively) such that A/B>1. This aspect ratio of the crystals is believed to enhance deposition of the structured benefit agent (see FIG. 3). The length is to be understood as the longer of the two dimensions when considering both length and width.

The structured benefit agents of the invention have been found to deposit much better from the compositions than if the benefit agent is not structured. Again, while not wishing to be bound by theory, deposition is believed to occur by direct transfer where the affinity of the structured benefit agent for surfaces is related to the properties of the crystals (e.g., aspect ratio) used to structure.

The structured benefit agent can be seen as a premix since it is a critical aspect of the invention that the benefit agent that is being structured and the crystalline structurant forming the "structure" be combined before adding to the carrying composition in which the structured benefit agent will be used. In this sense, the premix or structured benefit agent is acting as a vehicle for delivery of the benefit agent. On the other hand, the structured benefit agent may also enhance deposition of other benefit agents either by entrapping these benefit agents in a network formed by the structured benefit agent (if other benefit agent is in premix for example) or even if the other benefit agent is separately added to the composition separate from the premix.

The structured benefit agent vehicle thus specifically comprises:
(a) 0.1 to 99.5%, preferably 0.5 to 99.5% by wt. (including all ranges subsumed therein) of the vehicle of one or more benefit agents or mixtures thereof; and
(b) 99.9 to 0.1, preferably 99.5 to 0.5% by wt. (including all ranges subsumed therein) of the vehicle of crystalline structurant selected from the group consisting of crystalline materials (e.g., hydrogenated oils, fats, fatty acids, and fatty alcohols).

Benefit Agent

The benefit agent of the subject invention may be a single benefit agent component. Further the benefit agent may be a mixture of two or more components, one or all of which may have a beneficial aspect.

As noted, a separate benefit agent may also have enhanced deposition, even if it is not clear this is due to structuring or because it is entrapped in a network. Further, the structured benefit agent may enhance deposition of a benefit agent which is separately added (see, for example, applicants' co-pending application which is hereby incorporated by reference relating to enhanced hydrophilic benefit agent deposition).

The benefit agents can be emollients, moisturizers, anti-aging agents, skin-toning agents, skin lightening agents, sun screens etc.

The preferred list of benefit agents include:
(a) silicone oils, gums and modifications thereof such as linear and cyclic polydimethylsiloxanes; amino, alkyl alkylaryl and aryl silicone oils;
(b) fats and oils including natural fats and oils such as jojoba, soybean, sunflower seed oil, rice bran, avocado, almond, olive, sesame, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;
(c) waxes such as carnauba, spermaceti, beeswax, lanolin and derivatives thereof;
(d) hydrophobic plant extracts;
(e) hydrocarbons such as liquid paraffins, petrolatum, vaseline, microcrystalline wax, ceresin, squalene, pristan, paraffin wax and mineral oil;
(e) higher fatty acids such as behenic, oleic, linoleic, linolenic, lanolic, isostearic and poly unsaturated fatty acids (PUFA);
(g) higher alcohols such as lauryl, cetyl, stearyl, oleyl, behenyl, cholesterol and 2-hexydecanol alcohol;
(h) esters such as cetyl octanoate, myristyl lactate, cetyl lactate, isopropyl myristate, myristyl myristate, isopropyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;
(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;
(j) lipids such as cholesterol, ceramides, sucrose esters and pseudo-ceramides as described in European Patent Specification No. 556,957;
(k) vitamins such as vitamin A and E, and vitamin alkyl esters, including those vitamin C alkyl esters;
(l) sunscreens such as octyl methoxyl cinnamate (Parsol MCX) octocrylene(2-ethylhexyl 2-cyano-3,3-diphenylacrylate), octyl salicylate (2 ethylhexyl salicylate), benzophenone-3 (2-hydroxy-4-methoxy benzophenone), and avobenzone (4-tert-butyl-4'-methoxydibenzoylmethane) (these are merely illustrative);
(m) phospholipids;
(n) particles having a wide range of shapes, surface characteristics, and hardness characteristics which can be utilized to provide optical effect. Water-insoluble particles can be derived from a wide variety of materials including those derived from inorganic, organic, natural, and synthetic sources. Non-limiting examples of these materials include those selected from the group consisting of almond meal, alumina, aluminum oxide, titanium dioxide, mica, coated mica, sodium stearate, stearic acid, zinc stearate, aluminum silicate, apricot seed powder, aftapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e., polytetrafluoroethylene), polyhalogenated olefins, pumice rice bran, rye flour, sericite, silica, silk sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like;

(o) anti-aging, wrinkle-reducing, skin whitening, anti-acne, and sebum reduction agents such as alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives;

(p) fragrance molecules which include acetanisol; amyl acetate; anisic aldehyde; anisole; anisylalcohol; benzaldehyde; benzyl acetate; benzyl acetone; benzyl alcohol; benzyl formate; hexenol; laevo-carveol; d-carvone; cinnamaldehyde; cinnamic alcohol; cinnamyl acetate; cinnamyl formate; cis-3-hexenyl acetate; Cyclal C (2,4-dimethyl-3-cyclohexen-1-carbaldehyde);

dihydroxyindole; dimethyl benzyl carbinol; ethyl acetate; ethyl acetoacetate; ethyl butanoate; ethyl butyrate; ethyl vanillin; tricyclo decenyl propionate; furfural; hexanal; hexenol; hydratropic alcohol; hydroxycitronellal; indole; isoamyl alcohol; isopulegyl acetate; isoquinoline; ligustral; linalool oxide; methyl acetophenone; methyl amyl ketone; methyl anthranilate; methyl benzoate; methyl benzyl acetate; methyl heptenone; methyl heptyl ketone; methyl phenyl carbinyl acetate; methyl salicylate; octalactone; para-cresol; para-methoxy acetophenone; para-methyl acetophenone; phenethylalcohol; phenoxy ethanol; phenyl acetaldehyde; phenyl ethyl acetate; phenyl ethyl alcohol; prenyl acetate; propyl butyrate; safrole; vanillin; viridine, allyl caproate, allyl heptoate, anisole, camphene, carvacrol, carvone, citral, citronellal, citronellol, citronellyl acetate, citronellyl nitrile, coumarin, cyclohexyl ethylacetate, p-cymene, decanal, dihydromyrcenol, dihydromyrcenyl acetate, dimethyl octanol, ethyllinalool, ethylhexyl ketone, eucalyptol, fenchyl acetate, geraniol, gernyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, napthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, verdox, allyl cyclohexane propionate, ambrettolide, Ambrox DL (dodecahydro-3a,6,6,9a-tetramethyl-naphtho[2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, citronellyl isobutyrate, citronellyl propionate, cuminic aldehyde, cyclohexylsalicylate, cyclamen aldehyde, dihydro isojamonate, diphenyl methane, diphenyl oxide, dodecanal, dodecalactone, ethylene brassylate, ethylmethyl phenylglycidate, ethyl undecylenate, exaltolide, Galoxilide™ (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, γ-ionone, α-irone, isobutyl benzoate, isobutyl quinoline, Iso E Super™ (7-acettl,1,2,3,4,5,6,7,8-octahydro,1,1,6,7-tetramethyl napthalene), cis-jasmone, lilial, linalyl benzoate, 20methoxy naphthaline, methyl cinnamate, methyl eugenol, γ-methylionone, methyl linolate, methyl linolenate, musk indanone, musk ketone, musk tibetine, myristicin, neryl acetate, δ-nonalactone, γ-nonalactone, patchouli alcohol, phantolide, phenylethyl benzoate, phenylethylphenylacetate, phenyl heptanol, phenyl hexanol, α-santalol, thibetolide, tonalid, δ-undecalactone, γ-undecalactone, vertenex, vetiveryl acetate, yara-yara, ylangene;

(q) mixture of any of the benefit agents above.

To the extent materials above are hydrophobic, they are delivered as part of the premix (and more probably, although not necessarily, are structured; that is, at least one hydrophobic benefit agent will be structured, but others may be entrapped in the benefit agent network). Although not listed above, hydrophilic benefit agents may also be entrapped in the structured benefit agent network of the premix or separately added outside the premix. This is discussed, for example, in applicants' copending application relating to hydrophilic benefit agents hereby incorporated by reference into the subject application.

Crystalline Structurant

The crystalline structurant used for "structuring" the benefit agent oil or emollient of the subject invention may be a natural or synthetic hydrogenated oil or fat. Hydrogenated oils are also commonly referred to as fats. Hydrogenated oils and fats are further classified into their animal or vegetable origin. In addition some fatty acids and fatty alcohols can be used as structurant as well as salts of fatty acids, hydroxy fatty acids and fatty acid esters.

Hydrogenated oils are prepared by the catalyst-induced reaction of unsaturated double bonds in the fatty acid chains of the oils with hydrogen. Oils are fully or partially hydrogenated to make them more solid and to improve their stability against oxidation. Hydrogenated oils are wax-like, hard and can be brittle. They are compatible with oils and when mixed with oils at high temperature will cool to form solid masses.

Hydrogenated oils can be hydrogenated vegetable oils, hydrogenated coconut oil, hydrogenated palm kernel oil, hydrogenated rapeseed oil and many others. Another hydrogenated oil is castorwax. Castorwax is prepared from the hydrogenation of castor oil to create a hard, high melting, wax-like material.

It is well known that triglyceride fats have characteristic polymorphic crystals. Of the three polymorphic forms of crystals for triglycerides (alpha, beta prime and beta) the beta prime crystals are the smallest (<1 μm).

Along with size and shape, a high concentration of particles is required so that the crystals interact in the dispersion. Above a certain critical volume fraction of crystals, these interactions will lead to a buildup of a network that extends throughout the whole volume. The crystal network creates a solid-like material having viscoelastic properties.

Thus, the ability of the fat crystals of the hydrogenated oils to form continuous networks that entrap the oil depends on the solid fat content in the fat/oil mixtures and also on crystal morphology. For example, when there is a high concentration of beta prime crystals, a continuous network of small crystals extends through the sample and the sample is solid and stable. Typically, at solid fat contents of 40-50%, the consistency is hard and brittle, at 20-30% the system is solid-like but yielding, at lower concentrations the consistency is more fluid often with a grainy texture and at very low concentrations the fat crystals separate from the liquid. However, the exact concentrations of crystals required to build desired structures varies depending on the fat and oil used. In practice, the crystal formation is also dependent on processing conditions such as temperature, crystal formation rate and shearing.

A sample of various fats and hydrogenated oils that may be used according to the subject invention and their melting point temperature is set forth below in Table 1.

TABLE 1

Properties of Hydrogenated Oils, Fatty Alcohols and Fatty Acids

| Hydrogenated Oil/Fat | Manufacturer | Melting Point (° C.) |
| --- | --- | --- |
| Castorwax | CasChem | 70 |
| Stearine | Loders Croklaan | 60 |
| Alkofine R | Karlshamns | 60 |
| Lipex 408 | Karlshamns | 50 |
| Hydrogenated Palm Kernel Oil | Karlshamns | 35 |
| Hydrogenated coconut oil | Karlshamns | 42 |
| Stearyl alcohol | Aldrich | 54 |
| Stearic acid | Sigma | 53 |

Crystalline long chain fatty acids and long chain fatty alcohols can also be used to structure benefit agents. Examples of fatty acids are myristic acid, palmitic acid, stearic acid, arachidic acid and behenic acid. Examples of fatty alcohols are palmityl alcohol, stearyl alcohol, arachyl alcohol and behenyl alcohol. Some crystalline fatty acid esters and glyceride esters will also provide structuring benefit.

In addition, the crystalline materials can be combined with other structuring materials such as natural and synthetic waxes to form composite networks to structure benefit agents.

Structured Benefit Agent

As noted above, the structurant in the benefit agent is believed to form a three-dimensional supporting network which is believed to make the structured benefit agent more than just thickened benefit agents. That is, it changes the consistency of the fluid benefit agent (e.g., oil) to a solid-like material having good spreading/deposition properties. Deposition is believed to occur by the transfer of structured benefit agent droplets/particles to the substrate surface from the composition where the crystalline structure of the structuring material crystals (e.g., aspect ratio) is believed to help enhance affinity of the structured benefit agent to the substrate.

Other benefit agents in the premix may also structure (i.e., 2 or more) or just one may structure and/or the other benefit agent may have enhanced deposition by being entrapped in the network formed by the structured benefit agent.

The benefit agent may comprise 0.1 to 99.9% by wt. of the delivery vehicle/premix and structurant may comprise 99.9 to 1% by wt. of the delivery vehicle. Preferably benefit agent is 0.5 to 99.5%, more preferably 1 to 99% of vehicle. In some preferred embodiment, benefit agent comprises 50-99% of vehicle while structurant is 1 to 50%, preferably 2 to 45% of benefit agent vehicle.

When used, for example, as part of a cleanser emulsion where structuring material (e.g., hydrogenated oil) is 20% of benefit agent phase, droplet diameters of the structured benefit agent may be in the range of 1-15 µm, with average droplets having a size of 4-8 µm. Although there is no requirement that droplets must be of this size.

When incorporated into liquid cleanser formulations, the structured benefit agent droplets are generally solid when stored at room temperature and may be seen as particles. The droplets may be somewhat spherical but have a rough, textured surface, a result of the structurant crystal within the drops.

As mentioned, there is no large size requirement for the structured benefit agent droplets of the invention. Unlike prior art, the structured benefit agents can deposit high benefit agent amounts even at small droplet sizes, i.e., below 10 µm and possibly even submicron.

As also mentioned, low levels (<50% of structured benefit agent) of structurant can be used.

Figure 3:
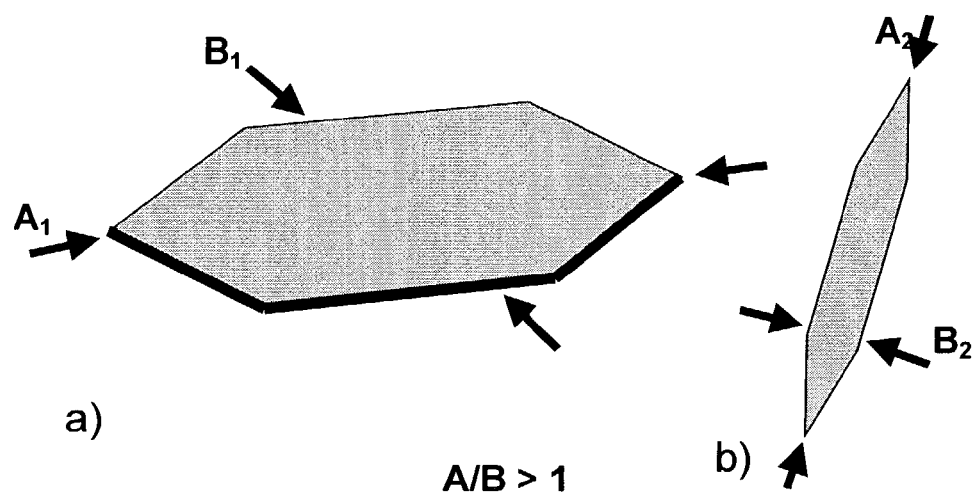
FIGS. 3a and 3b are schematics of a typical crystal structurants of the invention having length "A" and width "B". As noted, the aspect or axial ratio of A/B must be greater than 1. The length is to be understood as the longer of the two dimensions when considering length and width.
Figure 4:
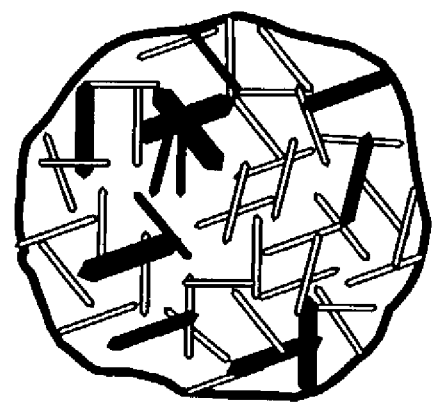
FIG. 4 is a schematic of structurant crystals (which can be "plate-like") forming a three-dimensional network within the structured benefit agent (e.g., oil)).

The only criticality is that the shape of the structurant has high axial or aspect ratio (A/B>1). This is shown in FIG. 3. The length is to be understood as the longer of the two dimensions when considering length and width. The fact that structuring exists is shown by high yield stress observed on benefit agents even when using low amount of benefit agent structurant (see FIG. 1).

The structured benefit agent of the invention may also be used in combination with other materials that have been shown to enhance the deposition of hydrophobic benefit agents (e.g., cationic polymers, inorganic thickening agents such as clays or silicas, and polymer thickening agents).

Finally, as noted, the structured benefit agent may enhance deposition of other non-structured benefit agents which are not part of a premix. This phenomenon is described, for example in one of applicants co-filed, co-pending applications.

Process

A critical aspect of the subject invention is that the benefit agent and crystalline structurant must be intimately combined (e.g., in a premix) before they are combined with the carrying composition. The combination of such premix with carrying composition should be when the structured benefit agent is molten, semi-molten or solid state. If used in molten or semi-molten state, it may be preferred that the viscosity of the structured benefit agent premix when mixing be no higher than about 250 Pa-s, more preferably 200 Pa-s, most preferable 150 Pa-s.

In one embodiment of the invention, the crystalline structurant and benefit agent (e.g., an emollient oil such as sunflower seed oil) are combined and may be heated to a temperature above the melting point of the structurant. These are then preferably mixed to uniformity.

Preferably, the molten material is added to a carrying composition, preferably a surfactant containing, personal product carrying composition at a temperature close to that of the benefit agent and structurant mixture. After mixing (about 10 seconds to an hour, preferably 5 minutes to 45 minutes), the mixture is cooled, if necessary, to room temperature. As noted, structurant is combined with benefit agent before addition to the carrying composition (e.g., aqueous surfactant phase). It should be noted that a pourable viscosity may also be obtained by vigorous mixing of structurant and benefit agent and that heating is not necessarily required.

When such process is followed, the resulting structured benefit agent compositions will have the properties described above (i.e. shear thinning, yield stress etc.) and provide deposition of benefit agent, when measured from the final carrying composition, of at least 5% greater, preferably at least 10% greater relative to level of deposition of benefit agent to substrate from final composition of the same benefit agent which is not structured according to process of the invention, or relative to a benefit agent which is not in the presence, in the final formulation, of such a structured benefit agent.

In one embodiment, when measured from the liquid carrying composition, a benefit agent oil will have deposition of at least about 60 µg/cm², preferably at least about 75 µg/cm², more preferably at least about 100 µg/cm². In another embodiment, when measured from a bar, benefit agent oil will have deposition of oil of at least about 5 µg/cm².

The absolute level of hydrogenated benefit agent, its proportion in a bar formulation relative to a low viscosity oily benefit material, and the process specifications, can all be adjusted in order to achieve the desired delivery to skin and the desired bar properties and user sensory properties.

Compositions

In one embodiment of the invention, the premix comprising oil/benefit agent may be used in a liquid (e.g., personal wash cleanser) composition. Typically, such composition comprises as follows:

(1) 0% to 99%, preferably 1 to 75% by wt. of a surfactant selected from the group consisting of anionic, amphoteric, nonionic and cationic surfactant and mixtures thereof;

(2) 0.1% to 90%, preferably 0.5% to 80% of a delivery vehicle comprising 0.1 to 99.9% delivery vehicle benefit agent or agents and 99.9 to 0.1% delivery vehicle crystalline structurant(s) selected from the group consisting of hydrogenated oils, fats and fatty acids and fatty alcohols;

(3) optional ingredients for liquid personal cleanser; and (4) balance water, wherein the premix (structured benefit agent) is delivered to liquid compositions as a separate premix; and wherein deposition of oil from the composition onto substrate is greater than 5%, preferably greater than 10% relative to deposition of same benefit agent not present in accordance with the invention.

In the specific liquid embodiment noted above, oil benefit agents will have deposition onto substrate of greater than 60 µg/cm².

In another embodiment of the invention, the premix comprising oil/benefit agent may be used in a bar (e.g., personal cleansing bar) composition. Typically, such composition comprises as follows:

(1) 1 to 80%, preferably 3 to 65% by wt. of a surfactant selected from the group consisting of anionic, amphoteric, nonionic and cationic surfactant and mixtures thereof;

(2) 0.1% to 90%, preferably 0.5% to 80% of a delivery vehicle comprising 0.1 to 99.9% delivery vehicle benefit agent or agents and 99.9 to 0.1% delivery vehicle crystalline structurant(s) selected from the group consisting of natural and synthetic hydrogenated oil, fats, fatty acids and fatty alcohols;

(3) 0.1 to 80%, preferably 5% to 70% by wt. total composition a structuring aid and/or filler;

(4) optional ingredients for personal cleansing bar, wherein the premix (structured benefit agent) is incorporated into bar compositions as a separate premix; and wherein deposition of benefit agent from the bar composition onto substrate is greater than 5%, preferably greater than 10% relative to deposition of same benefit agent not prepared in accordance with the invention.

In the specific bar embodiment noted, oil benefit agents will have deposition onto substrate of greater than 5 µg/cm².

Surfactant System (for Liquids or Bars)

Anionic Surfactants

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

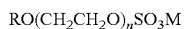

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sulfosuccinates may be monoalkyl sulfosuccinates having the formula:

$R^{40}{}_2CCH_2CH(SO_3M)CO_2M$;

amido-MEA sulfosuccinates of the formula $R^4CONHCH_2CH_2O_2CCH_2CH(SO_3M)CO_2M$ wherein $R^4$ ranges from $C_8$-$C_{22}$ alkyl and M is a solubilizing cation;

amido-MIPA sulfosuccinates of formula $RCONH(CH_2)CH(CH_3)(SO_3M)CO_2M$ where M is as defined above.

Also included are the alkoxylated citrate sulfosuccinates; and alkoxylated sulfosuccinates such as the following:

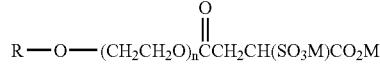

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $R^2CONR^3CH_2CH_2SO_3M$ wherein $R^2$ ranges from $C_8$-$C_{20}$ alkyl, $R^3$ ranges from $C_1$-$C_4$ alkyl and M is a solubilizing cation.

Another class of anionics are carboxylates such as follows:

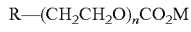

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5-15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application.

Another surfactant which may be used are $C_8$ to $C_{22}$ neutralized fatty acids (soap). Preferably, the soap used are straight chain, saturated $C_{12}$ to $C_{18}$ neutralized fatty acids.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

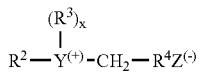

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxy-pentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

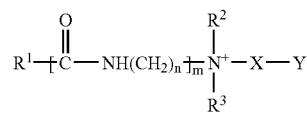

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

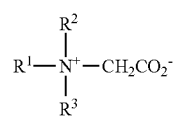

and amido betaines of formula:

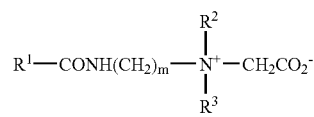

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

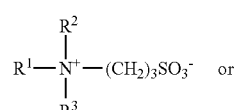   or

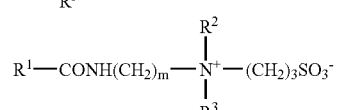

where m is 2 or 3, or variants of these in which —$(CH_2)_3SO^-_3$ is replaced by

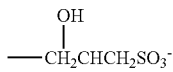

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 5% to 15% of the composition.

In addition to one or more anionic and optional amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

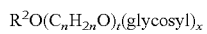

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Structurant Benefit Agent Premix

The benefit agent may be any of the benefit agents described previously in the section relating to the benefit agent.

Similarly, the crystalline structurant may be any one of the materials described above.

The premix/delivery vehicle is also as described above.

As indicated earlier, the premix should be made separately and, it can be a liquid (molten), semi-molten or solid state before adding to the final carrying composition. When used in a liquid composition the premix preferably may be in a pourable or flowable state (viscosity lower than 250 Pa-s, more preferably lower than 200 Pa-s, most preferably lower than 150 Pa-s before adding the final composition.

When using the benefit agent premix of the invention (either structuring benefit agent or being in the presence of benefit agent, even if added separately from premix), the benefit agent will deposit in an amount at least 5% or greater, preferably at least 10% greater than if no structured benefit agent is present in the final formulation.

In one embodiment, when used in a liquid composition, a benefit agent oil will have deposition of greater than 60 μg/cm², preferably greater than 75 μg/cm², more preferably greater than 100 μg/cm² and this deposition is not dependent on large droplet size of the structured benefit agent.

In a second embodiment when used in a bar composition, a benefit agent oil will have deposition of greater than 5 μg/cm² and this deposition is not dependent on large droplet size of the structured benefit agent.

Bar Compositions

Structuring Aids or Fillers

The compositions may also contain 0.1 to 80% by wt., preferably 5 to 70% by wt. of a structurant and/or filler. Such structurants can be used to enhance the bar integrity, improve the processing properties, and enhance desired user sensory profiles.

The structurant is generally long chain, preferably straight and saturated, ($C_8$-$C_{24}$) fatty acid or salt thereof or ester derivative thereof; and/or branched long chain, preferably straight and saturated, ($C_8$-$C_{24}$) alcohol or ether derivatives thereof.

A preferred bar structurant is polyalkylene glycol with molecular weight between 2000 and 20,000, preferably between 3000 and 10,000. Those PEGs are commercially available, such as those marketed under the tradename of CARBOWAX SENTRY PEG8000® or PEG4000® by Union Carbide.

Other ingredients that can be used as structurants or fillers include starches, preferably water soluble starches such as maltodextrin and polyethylene wax or paraffin wax.

Structuring aids can also be selected from water soluble polymers chemically modified with hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® (PEG modified glyceryl cocoate, palmate or tallowate) from Rewo Chemicals.

Other structuring aids which may be used include Amerchol Polymer HM 1500 (Nonoxynyl Hydroethyl Cellulose). 12-Hydroxy stearic acid may be used as a component of the bar structuring system. Such structurant is described, for example in U.S. Pat. No. 6,458,751 to Abbas et al., hereby incorporated by reference into the subject application.

Other Bar Ingredients

In addition, the bar compositions of the invention may include 0 to 15% by wt. optional ingredients as follows:

Perfumes (as described in section on benefit agents); sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers which may be used include Quatrisoft LM-200 Polyquaternium-24, Merquat Plus 3330—Polyquaternium 39; and Jaguar® type cationics.

Polyethylene glycols as conditioners which may be used include:

| Polyox | WSR-205   | PEG 14M,   |
| Polyox | WSR-N-60K | PEG 45M, or |
| Polyox | WSR-N-750 | PEG 7M.    |

Another ingredient which may be included are exfoliants such as polyoxyethylene beads, walnut shells and apricot seeds.

Cationic polymers, like other benefit agents, may be included in the bar surfactant/structurant filler carrying composition or they may be added into the premix benefit delivery vehicle along with the wax.

Typically, bars will also comprise 1 to 30%, preferably 2 to 20% water. The amount of water may vary depending on type of process and structuring material used.

Non Bar Composition

The non-bar, preferably liquid compositions of the invention may include optional ingredients as follows:

Another optional element of the invention is an emulsion stabilizer (found in, for example, liquid aqueous phase). The dispersion stabilizer is intended to provide adequate storage stability to the composition (i.e., so the benefit agent delivery vehicle is stable in the composition). The structured composition otherwise may be prone to separate under the action of gravity (creaming or sedimentation depending upon its density). The structured composition of the invention may also be prone to sticking together and coalescing.

The most effective dispersion stabilizers are those that can provide an adequate structure to the liquid, e.g., aqueous phase to immobilize the droplets thus preventing both gravitational separation and collision with other droplets. However, if the dispersion is too stable, the droplets of structured composition are inhibited from coming into proximity with the skin and thus effectively depositing. Therefore, the most effective dispersion stabilizers provided have excellent stability in the container but lose their effectiveness in immobilizing the structured benefit agent when they are applied to wet skin.

Aqueous dispersion stabilizers useful in the instant invention can be organic, inorganic or polymeric stabilizers. Specifically, the compositions comprise 0.1 to 10% by wt. of an organic, inorganic or polymeric stabilizer which should provide physical stability of the large structured oil droplets in the surfactant composition at 40° C. for over four weeks.

Inorganic dispersion stabilizers suitable for the invention include, but are not limited to clays, and silicas. Examples of clays include smectite clay selected from the group consisting of bentonite and hectorite and mixtures thereof. Synthetic hectorite (laponite) clay used in conjunction with an electrolyte salt capable of causing the clay to thicken (alkali and alkaline earth salts such as halides, ammonium salts and sulfates) particularly useful. Bentonite is a colloidal aluminum clay sulfate. Examples of silica include amorphous silica selected from the group consisting of fumed silica and precipitated silica and mixtures thereof.

Organic dispersion stabilizers are defined here as organic molecules that have a molecular weight generally lower than 1000 Daltons and form a network in the aqueous phase that immobilizes the dispersed structured oil phase. This network is comprised either of amorphous solids, crystals, or liquid crystalline phase. Suitable organic dispersion stabilizers for the instant invention are well know in the art and include, but are not limited to any of several types of long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof.

Another example of organic dispersion stabilizer are alkanolamides having from about 14 to about 22 carbon atoms. Preferred alkanolamides are stearic monoethanolamide, stearic diethanolamide stearic monoisopropanolamide, stearic monoethanolamide stearate and mixtures thereof.

Still another class of useful dispersion stabilizer is long chain fatty acid esters such as stearyl stearate, stearyl palmitate, palmityl palmitate, trihydroxystearylglycerol and tristearylglycerol.

Another type of organic dispersion stabilizer is the so-called emulsifying waxes such as mixtures of cetostearyl alcohol with polysorbate 60, cetomacriogol 1000, cetrimide; a mixture of glycerol monostearate with a stearic soap, and partially neutralized stearic acid (to form a stearate gel).

Still another example of a suitable dispersion stabilizing agent is long chain amine oxides having from about 14 to about 22 carbon atoms. Preferred amine oxides are hexadecyldimethylamine oxide and octadecyldimethylamide oxide.

Example of a suitable polymeric dispersion stabilizing agents useful in the present invention include: carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, carrageenan, hydroxymethyl carboxypropyl cellulose, methyl cellulose, ethyl cellulose, guar gum (including cationic guar gums), gum karaya, gum tragacanth, gum arabic, gum acacia, gum agar, xanthan gum and mixtures thereof. Preferred carbohydrate gums are the cellulose gums and xanthan gum.

An especially preferred types of polymeric dispersion stabilizer agent include acrylate containing homo and copolymers. Examples include the crosslinked poly acrylates sold by B.F. Goodrich under the CARBOPOL trade name; the hydrophobically modified cross linked polyacrylates sold by B.F. Goodrich under the PEMULEN trade name; and the alkali swellable acrylic latex polymers sold by Rohm and Haas under the ARYSOL® or ACULYN® trade names.

The above dispersion stabilizers can be used alone or in mixtures and may be present in an amount from about 0.1 wt. % to about 10 wt. % of the composition.

Perfume, which may be the combination of several fragrances, may be selected on the basis of the ability of the fragrances to be incorporated into the benefit agent delivery vehicle to provide enhanced fragrance delivery/benefit(s). However, as noted, perfume may also comprise a separate benefit agent which may be entrapped in a network formed by different structured benefit agent or may be added separately to the composition and not as part of the premix.

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and Vitamin A, C & E or their derivatives may be used advantageously in amounts of about 0.01% or higher if appropriate.

Polyethylene glycols which may be used include:

| Polyox | WSR-205 | PEG 14M, |
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, walnut sheets and apricot seeds Another preferred ingredient is a crystallization suppressant or control agent which is used to suppress individual or mixtures of sunscreen ingredients from crystallizing out of solution. This may lead to reduced deposition. These suppression agents include, for example, organic esters such as $C_{10}$-$C_{24}$, preferably $C_{12}$-$C_{15}$ alkyl benzoate among others. Other examples include Bernel PCM from Bernel, and Elefac 205 from Bernel. Specific sunscreen(s) are more resistant to crystallization than others, e.g., butyl octyl salicylate.

Except in the operating and comparative examples, or where otherwise explicitly 11 indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Protocol

Ingredients Used

Sodium lauryl ether sulfate (SLES) was Steol CS330 from Stepan Co. (Northfield, Ill.). Cocamidopropyl betaine (CAPB) was Tego Betaine F50 from Goldschmidt Chemical Corp. (Hopewell, Va.). Refined sunflower seed oil was supplied by Welch, Holme and Clark Co., Inc. (Newark, N.J.). The petrolatum was white petrolatum from Penreco (Karns City, Pa.). The hydrogenated oils are commercially available from many manufacturers and were directly added to the formulations without further modification. Hydrogenated coconut, palm kernel, rapeseed and vegetable oils were supplied by Jarchem Industries, Inc. (Newark, N.J.). Castorwax was supplied by CasChem, Inc. (Bayonne, N.J.) Hydrogenated cotton seed oil, Stearine 07 was supplied by Loders Croklaan. The commercially available AquaPel 15L from ExxonMobil Chemical (Edison, N.J.) is a linear butadiene-isoprene copolymer ($M_w$ 15,000).

Other materials used in the production of example bar formulations were as follows: propylene glycol supplied by Ruger Chemical Company; Pricerine 4911 palmitic-stearic acid supplied by Uniqema; sodium cocoyl isethionate and 82/18 soap supplied by Lever; Mackam 1L supplied by McIntyre Group Ltd.; Emery 916 glycerine supplied by Cognis Corporation; Superhartolan by Croda; and polyethylene glycols from the Pluracol series supplied by BASF.

Non-Bar Skin Cleanser Base

| Component | % wt. |
|---|---|
| Sodium Laureth Sulphate | 13.0 |
| Cocamidopropyl Betaine | 7.0 |
| Di Water | To 100.0 |
| Ph = 6.0-7.0 | |

Equipment Processing

Small batches of liquid cleanser prototypes were mixed using an overhead stirrer equipped with a high-efficiency paddle. Formulations were prepared in 250 ml stainless steel beakers which were placed in a thermally-controlled water bath (±1.0° C.).

Preparation of Structured Benefit Agent

Structured (e.g., hydrogenated oil structured) benefit agent premixes (delivery vehicles) were prepared at temperatures at or just above the melting points of the structurant or other mixtures of benefit agent structuring component. Typically, the structuring material was weighed into a 125 ml stainless steel beaker and then the appropriate amount of benefit agent (e.g., sunflower seed oil) was added based on the formulation specifications. The components were then heated by placing the beaker in a thermally-controlled water bath to melt the structuring material (e.g., hydrogenated oil). The molten structured oil was stirred with a sigma blade mixer until uniformly mixed and, for liquid compositions, maintained at the elevated temperature until use (usually no more than 5 min). For bar compositions, the mixture was then either maintained at elevated temperature until its incorporation into a base formulation (i.e. a mixture of surfactants and bar structuring aids), or was allowed to cool to ambient temperature for incorporation into a bar base formulation.

Preparation of Liquid Prototype Samples

Liquid cleanser formulations were prepared under similar processing conditions except for differences in mixing temperatures as necessary due to the varying melting temperatures of the structurants. Formulations were prepared in 250 ml stainless steel beakers immersed in a thermally-controlled water bath. First the SLES and CAPB along with additional water were added together and mixed at 100 to 150 rpm for 5 min using an overhead stirrer. Mixing was continued until homogeneous while the temperature was raised to that of the wax-oil premix. Just prior to addition of the oil phase, the mixing speed was increased to 250 rpm. The molten structured oil premix was then poured into the stirring surfactant mixture and stirred (about 20 minutes) while maintaining the elevated temperature. When mixing was completed, the finished product was removed from the temperature bath and allowed to cool to room temperature without further stirring. In the examples, component amounts are given as a weight percentage of the composition.

Preparation of Bar Prototypes.

Bars produced via a melt cast process route were made in Pyrex mixing vessels heated with electric heating mantles. Multiple turbine blades controlled with adjustable speed electric motors provided agitation for the vessel. Formulations were manually poured into polypropylene molds for cooling and solidification.

The base bar compositions were prepared by melting the bar structuring aids followed by addition of surfactants and then any additional components of the base formulation as required.

Bars produced via an extrusion process were mixed in a Patterson sigma blade mixer. The base bar carrying compositions were prepared by mixing components in the order described for the cast-melt process above.

The compositions were then passed over a chill roll set at 15° C. The flakes from the chill roll were then extruded through a Weber Seelander laboratory scale plodder. Bars were stamped on a Sigma Engineering air-driven press.

Silicone Rubber Surface Preparation (Silflo)

Silflo silicone rubber material (Flexico Developments, England) was used as received. Silflo replica surfaces for deposition trials were prepared with surface roughness to approximate the skin surface roughness. About 5 ml of Silflo material was squeezed from the stock bottle onto wax paper. After the addition of 2-3 drops of catalyst (supplied with the Silflo) the liquid material will thicken while mixing with a stainless steel spatula (about 30 seconds). A piece of 100 grit sandpaper was cut to 4×4 cm square and taped to a surface to leave approximately 2.5×2.5 cm exposed. The thickened material was spread evenly over the sandpaper and allowed to dry (about 10 min). Once set, the solid Silflo replica was separated by peeling away the sandpaper and covering the exposed adhesive side of the tape with new pieces of tape. The replica surface was a negative of the sandpaper surface and thus is textured. The 100 grit was chosen to approximate the surface roughness of skin.

Sunflower Seed Oil Deposition Protocol for Liquid Compositions

The amount of sunflower seed oil that deposits from the structured oil formulations was assessed on the Silflo replica surfaces. Newly prepared samples of formulations were tested in triplicate by applying product to the Silflo surface, rubbing in the product, rinsing and then extracting any oil remaining bound to the surface. In practice, 8.6 mg of product was applied per square centimeter of surface. After addition of one drop of tap water, the product was rubbed on the surface with one finger for 15 seconds (approximately 20 circular rubs). The surface was then rinsed with tap water maintained at 37° C. and a flow rate of 13-14 ml/sec, holding the sample 5 cm away from the tap at an angle of 45°. After rinse, the sample was blotted once with a towel and allowed to air dry for 15 min. The Silflo replica was then cut from the tape border with a razor blade and placed into a 20 ml glass vial with 10 g of hexanes. After mixing with an automatic "wrist action" shaker for 15 min, the Silflo replica was removed from the vial. For analysis of oil content, the extraction solvent was transferred to 1 ml glass vials.

Sunflower Seed Oil Deposition Protocol for Bar Compositions

Full thickness porcine skin was obtained from Sinclair Research Center, Inc. It was cut into pieces of size 8 cm×10 cm. The skin was shaved with a disposable razor, rinsed with warm water and then rinsed with ethyl alcohol (10 ml) and wiped dry with an absorbent paper towel. After cleaning in this manner, the skin was then hydrated for 10 seconds under running tap water set to 100° F. The amount of bar product applied to the skin was 3.3 mg/cm$^2$. Thus, the appropriate amount of bar material was weighed out according to the area of skin to be washed and then an equal amount of water was added to the bar sample and this was then allowed to sit for 15 min at ambient temperature in a covered vessel. The slurry so formed was then transferred onto the piece of skin to be washed and spread evenly over the entire surface using one hand covered with a textured latex glove. The skin was then washed over its entire area using the gloved hand, rubbing in a circular motion for 30 s. The skin was then rinsed under a tap for 10 seconds at a flow rate of 70 ml/minute and temperature of 100° F. Excess water was removed by patting the skin with a paper towel. The skin was then allowed to air dry at ambient temperature for 15 minutes. The sunflower seed oil that was deposited on the skin during the wash procedure was recovered by solvent extraction. A glass cylinder (7 cm$^2$ area) was firmly placed onto the skin surface and 2 ml of solvent (25:75 (v/v) chloroform:methanol) dispensed into the cylinder and stirred with a glass rod for 1 minute. The solvent was then transferred to a 10 ml vial using a disposable plastic pipette. The extraction process was repeated two more times and all three portions of the solvent were combined in the single vial. The sample was then filtered using a disposable syringe fitted with a 0.45 μm Millipore disposable filter. The solvent was evaporated under nitrogen.

Sunflower Seed Oil Deposition Analysis by Thin Layer Chromatography (TLC) for Liquid Compositions Analysis of oil concentration in the hexanes extracts was performed using thin layer chromatography (TLC). Samples were spotted onto TLC plates using an automatic TLC spotter (CAMAG Automatic TLC Sampler 4, CAMAG, Switzerland). Along with the sample extracts, six standard solutions of sunflower seed oil in hexanes were also spotted on each plate. Standards were prepared at concentrations ranging from 125 to 450 μg/g. TLC plates were cleaned before use by soaking first in methanol and then isopropanol for 15 min each and then dried overnight. After spotting, plates were placed in a glass TLC chamber containing 100 ml of developing solution (70% hexane, 29% ethyl ether, 1% acetic acid). When the solution had traveled % of the plate height, the plate was removed and air dried overnight. After drying, the TLC plates were immersed in staining solution (aqueous solution containing 10% cupric sulfate, 8% phosphoric acid). After blotting excess staining solution from the plates, they were heated for 30 min on a hotplate set at 165° C. For measurement of the deposited oil, the stained plates, now having charred spots representing the deposited oil extracted from the Silflo surfaces, were digitally scanned using a GS-700 Imaging Densitometer (Bio-Rad Laboratories, Hercules, Calif.). Using the scanning software, the intensity of the sample spots was calculated based on a standard curve generated for the 6 standards applied to the plate. From these apparent intensity values, the concentration of sunflower oil in the extracts was calculated.

Sunflower Seed Oil Deposition Analysis by High Performance Liquid Chromatography (HPLC for Bar Examples)

Quantification of the sunflower seed oil recovered from the deposition trials was via high performance liquid chromatography. Following evaporation of the solvent under nitrogen as described above, the sample was reconstituted in mobile phase solvent (70:30 (v/v) acetone:acetonitrile). LC separation was performed on a Hewlett-Packard Series 1100 HPLC. Detection was via a light-scattering detector, Alltech ELSD 2000. The column used for LC separation was a Waters Symmetry $C_{18}$ (39×150 mm) kept at 30° C. The mobile phase was 70:30 (v/v) acetone:acetonitrile. The flow rate was 0.8 ml/min. The sample injection volume was 100 μl. Run time was 18 min. Detector nitrogen flow rate was 0.9 L/min and evaporative tube temperature was 40° C. (with impactor OFF). The elution time for the peak of interest was about 6.2 min.

Standards were prepared at concentrations ranging from 10 to 40 ppm of sunflower seed oil. The level of sunflower oil in the extracts was calculated based on the standard curve generated from the standard solutions.

Droplet Size Measurement

Droplet size was measured from images captured of the oil droplets in the liquid formulations. Microscopic images were taken from samples of the body wash prototypes by placing a small amount (<0.1 ml) onto a glass slide. The sample was gently spread on the slide following placement of a cover slip. Samples were examined at 100× magnification using an optical microscope (Axioplan Model, Carl Zeiss, Inc., Thornwood, N.Y.). The microscope was equipped with a video camera, image processor and video monitor. The camera was connected to a personal computer and images were digitally captured using appropriate software. Using the imaging software, (structured) oil droplets were measured individually. At least 200 droplets were measured for each formulation sample.

Viscosity Shear Profile Measurement

The Rheometric Scientific ARES controlled strain rheometer (SR-5, RheometricScientific, Piscataway, N.J.) was used to determine shear profiles of structured benefit agents used herein. The rheometer was set up with parallel plates 25 mm in diameter typically with 200 to 500 μm gaps between the top and bottom plates. Test temperature was 37° C. Programmed steady shear rate sweeps were performed where the shear rates were logarithmically varied from 0.1 to 1000 seconds$^{-1}$, with 5 points recorded per decade. The shear scan typically takes 5 minutes to complete. The output is viscosity as a function of shear rate.

Yield Stress Measurement

The yield stress values of the structured benefit agents were measured using a Rheometric Scientific Stress Controlled Rheometer model SR-5 (Rheometric Scientific, Piscataway, N.J.). Stress ramp tests were performed on samples in stress ranges from 0.2 to 12000 Pa using either a 25 mm or 40 mm cone and plate fixture. Samples of the structured benefit agent to be tested were loaded between the fixture (top plate) and bottom plate. Using the RSI Orchestrator software supplied with the instrument, tests were conducted by incrementing the applied stress from 0.2 Pa to user defined final stress value. The user also sets testing time typically at 15 minutes. Tests are completed when the sample yields (flows), which is noted by a sharp decrease in sample viscosity as observed as the software plots the experimental data as the test is conducted. Yield stress values were determined from linear plots of the viscosity versus strain. The first data point after the peak of the curve is the yield value. Alternatively, lines can be fit to the linear portions of the curve before and after the peak. The intersection of the line will give the yield value. Yield stress can also be determined from semi-logarithmic plots of the viscosity (Pa-s) against stress (Pa). The yield value is the first data point for stress after the linear portion of the curve at lower stress values. The yield stress values here are to be understood as a critical yield stress value or the value of the stress where the material begins to flow.

Lather Generation Methods

Inverted Funnel

The bar and hands were placed under running tap water at 35° C. They were removed from the water and the bar rotated ten times. The bar was put down and lather was generated by rubbing the hands together ten times. The lather was collected under an inverted funnel in a large tub of water. A graduated cylinder attached to the end of the funnel was used to record the lather volume in millimeters.

Density-Mass-Volume (DMV)

The bar and hands were placed under running tap water at 35° C. They were removed from the water and the bar was rotated ten times. The bar was put down and lather was generated by rubbing the hands together ten times. The lather was collected in a large dish and weighed. The lather was then collected in a small petri dish of known volume. A spatula was used to carefully level the lather surface to the same height as the petri dish and the weight was recorded. The total weight of lather generated by a bar was recorded and converted to volume numbers using density measurement.

Bar Hardness Measurement

The hardness of the bar was measured using a 351 g cone-shaped penetrometer. The penetration depth (in mm) was measured 1 minute after the penetrometer is released.

Protocol for Assessment of Bar Mush

Bar mush was determined by placing the bar in a plastic dish and adding 25 ml of water. The dish was covered and remained untouched for 24 hours. The subsequent mush layer was gently scraped off with a spatula and the weight of the bar determined.

Protocol for Assessment of Bar Rate of Wear

A one half gallon container was placed under running tap water at 105° F. The hands and test bar were submerged in the water for 3 seconds, they were then removed and the bar was rotated in the hand ten times. The procedure was repeated and the bar was submerged a final time and stored in a flat bottom soap dish containing 7.5 ml water. The washing procedure was done four times on day one and one time on day two. The bar was left to dry overnight and the average grams per wash was calculated and reported.

Examples 1 and 2

Comparatives A-C

A requirement to achieve high deposition of benefit agent is to mix structurant(s) and benefit agent(s) prior to incorporation into formulations. To demonstrate the necessity of pre-mixing the structurant and benefit agent, liquid cleanser formulations were prepared where the structurant and benefit agent were prepared as a pre-mix and added to the formulation base. For comparison, liquid cleanser formulations were prepared using the same structurant and benefit agents except that these formulations were prepared by individually adding structurant and benefit agent directly to the formulation base without pre-mixing the structurant and benefit agent. Shower formulations were prepared having various compositions.

A liquid cleanser composition without benefit agent (sunflower seed oil) being structured (Comparative A) was prepared at room temperature. Using an overhead mechanical mixer equipped with a high efficiency stirrer and stirring at 250 rpm, 25% w/w of sunflower seed oil with 75% aqueous surfactant phase (comprising water and surfactants) were mixed.

Comparative A composition is set forth below:
Comparative A (Comparative, Control Skin Cleanser)

| Component | % wt. |
|---|---|
| Sodium Laureth Sulphate | 13.0 |
| Cocamidopropyl Betaine | 7.0 |
| Sunflower Seed Oil (unstructured) | 25.0 |
| Distilled Water | To 100.0 |
| Ph = 6.0-7.0 | |

Examples 1 and 2 were prepared by mixing 25% w/w of a structured benefit agent oil comprising a structurant such as hydrogenated rapeseed oil (Akofine R) or hydrogenated cottonseed oil (Stearine 07); and sunflower seed oil to the aqueous surfactant phase. For these formulations, the structured oil was prepared by addition of the structurant to the sunflower seed oil, heating the mixture to a temperature above the melting point of the structurant and mixing until uniform. The molten structured oil was only then combined with (e.g., added to) the aqueous surfactant phase which was maintained at the same temperature as the structured oil. After mixing for 15 minutes, the formulation was cooled to room temperature. The structurant must be, and was, added to the oil phase prior to dispersion of the structured oil phase into the aqueous surfactant phase.

An example of the composition of the invention is set forth below as Example 1.

Example 1 (Invention, Cleanser base, 5.0% hydrogenated rapeseed oil+20.0% sunflower seed oil)

| Composition | % Wt. |
|---|---|
| Sodium Laureth Sulphate | 13.0 |
| Cocamidopropyl Betaine | 7.0 |
| Hydrogenated rapeseed oil (Akofine R) | 5.0 |
| Sunflower Seed Oil | 20.0 |
| Distilled Water | To 100.0 |

Example 2 (Invention, Cleanser, 12.5% Stearine 07+12.5% sunflower seed oil) was prepared in the same way as Example 1 except the structurant was stearine (Stearine 07). That is, the example comprises the same formulation as Example 1 except that the structured oil comprises 12.5% hydrogenated cottonseed oil (Stearine 07) and 12.5% sunflower seed oil.

Comparative B (Comparative, Cleanser, 5.0% hydrogenated rapeseed oil+20.0% sunflower seed oil) comprises the same formulation as Example 1 including use of 5.0 wt. % hydrogenated rapeseed oil structurant. It differs from Example 1 only in that the 5.0% hydrogenated rapeseed oil and the sunflower seed oil were added separately into the surfactant phase.

Comparative C (Comparative, Cleanser, 12.5% Stearine 07+12.5% sunflower seed oil) comprises the same formulation as Example 2 and differs only in that the 12.5 wt. % stearine and sunflower seed oil were added separately into the aqueous surfactant phase.

TABLE 1

Sunflower Seed Oil Deposition from Formulations with Structured Oils

| Formulation | Deposition, μg/cm² |
|---|---|
| Comparative A (Comparative, no structurant) | 40 |
| Example 1 (Invention, Cleanser, 5.0% Akofine R + 20.0% sunflower seed oil) | 455 |
| Comparative B (Comparative, separate addition of Akofine R structurant and sunflower seed oil) | 95 |
| Example 2 (Invention, Cleanser, 12.5% Stearine 07 + 12.5% sunflower seed oil) | 1269 |
| Comparative C (Comparative, separate addition of structurant, Stearine 07 and sunflower seed oil) | 33 |

As seen from Table 1, the importance of the order of addition of the components to create the structured oil is demonstrated by comparing oil deposition from Examples 1 and 2 with formulations prepared from the same components but differing processing conditions. As seen clearly, Comparative B and C (separate addition of structurant and benefit agent oil) have far less deposition than the Examples 1 and 2. Comparatives B and C were prepared by the separate addition of structurant and sunflower seed oil to the aqueous surfactant phase. For these formulations, structurant, sunflower seed oil and 75 wt % of aqueous surfactant phase were heated in separate vessels to the same temperature which is above the melting point of the structurant. The sunflower seed oil was added to the aqueous surfactant phase and mixed with an overhead stirrer as described above. The structurant was then added separately to the mixture and the entire formulation was mixed for 15 minutes. After mixing, the formulation was cooled to room temperature.

Examples 3 and 4

Comparative D

Examples 3 and 4 and Comparative D are liquid cleansers that were prepared with the composition shown in Comparative A with the exception of the oil phase. For Examples 3 and 4 the sunflower seed oil was replaced with a mixture of a crystalline oil phase structurant and sunflower seed oil. Comparative D was prepared using a non-crystalline oil phase structurant added to sunflower seed oil. In each of these formulations the oil phase was prepared as a pre-mix (structurant and benefit agent oil) prior to addition of the oil phase to the aqueous surfactant base. This example is to demonstrate that to achieve high benefit agent deposition requires that the oil phase structurant is a crystalline material. In addition, the examples show other hydrogenated oils that can be used to structure the benefit agent oil.

Example 3 (Invention, Cleanser, 5% castorwax+20% sunflower seed oil) comprises the same formulation as Example 1 except that it uses 5 wt. % castorwax as structurant added to 20% sunflower seed oil instead of 5% hydrogenated rapeseed oil added to 20% sunflower seed oil. It is prepared as per the invention, i.e., structurant and oil mixed before addition to surfactant phase.

Example 4 (Invention, Cleanser, 12.5% Lipex 408+12.5% sunflower seed oil) comprises the same formulation as Example 1 except that it uses 12.5 wt % hydrogenated vegetable oil (Lipex 408) as structurant added to 12.5% sunflower seed oil instead of 5% hydrogenated rapeseed oil (Akofine R) added to 20% sunflower seed oil. Again, structurant and oil are combined before combining with surfactant phase.

The following comparative was also prepared.

Comparative D (Comparative, Cleanser with 10% polymer thickener, which is AquaPel 15, a linear copolymer of butadiene/isoprene+15% sunflower seed oil) uses a non-crystalline linear polymer used as a benefit agent (oil) structurant. It comprises the same formulation as Example 1 except that it uses 10% polymer thickener added to 15% sunflower seed oil. Again, structurant and oil are combined before combining with surfactant phase.

Comparative D

| Component | % Wt. |
| --- | --- |
| Sodium Laureth Sulphate | 13.0 |
| Cocamidopropyl Betaine | 7.0 |
| AquaPel 15L (copolymer of butadiene/isoprene) | 10.0 |
| Sunflower Seed Oil | 15.0 |
| Distilled Water | To 100.0 |

In Table 2, the benefit agent oil deposition from Examples 1-4 is listed along with deposition from Comparatives A and D. As shown in Table 2 only crystalline structurants (Examples 1-4) yield high deposition of 60 μg/cm² or greater. Comparative D, using a non crystalline material, fails to yield these results.

TABLE 2

Sunflower Seed Oil Deposition from Formulations with Structured Oils

| Formulation | Deposition, μg/cm² |
| --- | --- |
| Comparative A (Comparative, sunflower seed oil only)* | 0 |
| Example 1 (Invention, Akofine R)* | 455 |
| Example 2 (Invention, Stearine 07)* | 1269 |
| Example 3 (Invention, castorwax) | 1062 |
| Example 4 (Invention, Lipex 408) | 898 |
| Comparative D (Comparative, AquaPel 15L) | 51 |

*From previous Table 1

As seen only structurants of invention provide good deposition. Using no structurant (Comparative A) or non-crystalline structurant (Comparative D), fails to provide such deposition.

Examples 1-4

Droplet Size

As described, this invention places no requirement on large droplet size for high deposition of benefit agent. To demonstrate this, the droplet size was measured for the following examples of liquid cleansers that were prepared in accordance with the process of the invention as described above (i.e., benefit agent sunflower seed oil and structurant were first combined). Formulations prepared with structured benefit agent with crystalline structurants will deposit benefit agent on surfaces at high amounts when said structured benefit agents are at small droplet sizes (average droplet diameter <10 μm diameter).

Structured benefit agent oil droplet size and deposition results are set forth in Table 3 below:

TABLE 3

Sunflower Seed Oil Deposition from Liquid Cleanser Formulations with Structured Oils and Average Benefit Agent Oil Droplet Size

| Formulation | Average Droplet Diameter, μm | Deposition, μg/cm$^2$ |
|---|---|---|
| Example 1 (Invention) | 6.4 | 455 |
| Example 2 (Invention) | 7.6 | 1269 |
| Example 3 (Invention) | 6.2 | 1062 |
| Example 4 (Invention) | 5.6 | 898 |

As shown in Table 3, deposition was excellent for several different structurants and with average benefit agent oil droplet sizes much lower than that previously suggested for effective deposition. The best deposition of hydrophobic benefit agent by U.S. Pat. No. 6,066,608 suggests that droplets have average diameter larger than 200 μm; U.S. Pat. No. 5,854,293, suggests droplets larger than 500 μm, or U.S. Pat. No. 5,661,189, which suggests droplets from 50-500 μm.

Examples 5-11

In order to show that benefit agent oils can be structured using varying amounts of structurants (e.g., 0.2% to 12.5%) and that the level of deposition can be manipulated by amount of structurant, applicants prepared the following liquid cleanser formulations using Stearine 07 as the benefit agent oil structurant.

Example 5 (Invention, Cleanser with 0.2% Stearine 07+24.8% sunflower seed oil).

Example 6 (Invention, Cleanser with 1.3% Stearine 07+23.7% sunflower seed oil).

Example 7 (Invention, Cleanser with 2.5% Stearine 07+22.5% sunflower seed oil).

Example 8 (Invention, Cleanser with 3.8% Stearine 07+21.2% sunflower seed oil).

Example 9 (Invention, Cleanser with 5.0% Stearine 07+20.0% sunflower seed oil).

Example 10 (Invention, Cleanser with 6.2% Stearine 07+18.8% sunflower seed oil).

Example 11 (Invention, Cleanser with 10.0% Stearine 07+15.0% sunflower seed oil).

Deposition results for the various compositions are set forth in Table 4 below:

TABLE 4

Sunflower Seed Oil Deposition from Liquid Cleanser Formulations with Structured Oils

| Formulation | Stearine 07, % w/w | Deposition, µg/cm² |
|---|---|---|
| Example 5 | 0.2 | 7 |
| Example 6 | 1.3 | 149 |
| Example 7 | 2.5 | 649 |
| Example 8 | 3.8 | 884 |
| Example 9 | 5.0 | 1494 |
| Example 10 | 6.2 | 1534 |
| Example 11 | 10.0 | 1407 |
| Example 2* | 12.5 | 1269 |

*From Table 1

The structurant (Stearine 07) content is measured as percent of the overall composition. That is, for example, Example 9 combines 5% stearine with 20% sunflower seed oil in a premix which, when in molten state, is then combinable with the rest of the composition. As seen from Table 4, small or large amounts of structurant can be used to enhance deposition. However, critical concentrations of structurant exist to reach desired deposition levels. As seen from the increasing deposition as the amount of structurant increases, the level of structurant can be used to control the level of deposition. Thus the deposition can be tuned to the level that is desired for a given application.

Example 12 and Comparative E

Structuring of a benefit agent oil with a hydrogenated oil to provide enhanced deposition from a personal cleansing bar.

The cleansing bar formulation, Example 12, was produced via a melt-cast process. It was prepared by mixing 30% w/w of a structured oil (comprising 4.5% w/w of Stearine 07 as structurant) into a base bar formulation at 75° C. for 10-20 min. The mixture was then cooled to room temperature. In this case, the structured oil was prepared by addition of the structurant to the sunflower seed oil, heating the mixture to a temperature above the melting point of the structurant and mixing until uniform. The molten structured oil was only then combined with (i.e. added to) the molten surfactant base formulation which was maintained at the same temperature as the structured oil. After mixing for 10-20 min, the formulation was poured into a mold and cooled to room temperature. A cooling rate of 0.5 to 5.0° C./min was typically used to obtain high quality bars with excellent sensory and user properties. The structurant must be, and was, added to the oil phase prior to dispersion of the structured oil phase into the molten surfactant base formulation.

Comparative E is a similar formulation with the only difference being that 30% w/w of sunflower seed oil (not structured) was added to the base bar formulation.

These compositions of the invention are set forth below as Example 12 and Comparative E.

TABLE 5

Composition of Example 12 and Comparative E

| Component | Example 12 % wt | Comparative E % wt |
|---|---|---|
| Sodium cocoyl isethionate (from DEFI*) | 20.0 | 20.0 |
| Cocoamidopropyl betaine | 5.0 | 5.0 |
| Sunflower seed oil | 25.5 | 30.0 |
| Palmitic-Stearic acid | 16.4 | 16.4 |
| Sodium Stearate | 8.2 | 8.2 |
| Propylene Glycol | 5.0 | 5.0 |
| Stearine 07 | 4.5 | 0 |
| 82/18 tallow/coco soap | 2.8 | 2.8 |
| Water | 6.0 | 6.0 |
| Sodium isethionate | 1.9 | 1.9 |
| Coconut fatty acid | 1.2 | 1.2 |
| Sodium chloride | 0.7 | 0.7 |
| Titanium dioxide | 0.8 | 0.8 |
| Fragrance | 1.0 | 1.0 |
| EDTA | 0.02 | 0.02 |
| EHDP | 0.02 | 0.02 |

*DEFI: directly esterified fatty acid isethionate, which is a mixture containing about 74% by weight of fatty acid isethionates, 23% stearic-palmitic acid and small amounts of other materials, manufactured by Lever Brothers' Co., U.S.

Table 6 below sets forth the deposition results for each of the compositions.

TABLE 6

Sunflower Seed Oil Deposition from Example 12 and from Comparative E.

| Formulation | Deposition, µg/cm² |
|---|---|
| Example 12 | 7 |
| Comparative E (30% oil, no structurant) | 3 |

As can be seen clearly from Table 6, deposition of sunflower seed oil is significantly enhanced when it is structured with the Stearine 07 as in Example 12.

Example 13 and Comparative F

Structuring Triglyceride Oil with a Hydrogenated Oil for Improved Bar Properties The cleansing bar formulation, Example 13, was produced via a melt-cast process. It was prepared by mixing 20% w/w of a structured oil (comprising 5% w/w of the Stearine 07 structurant and sunflower seed oil) into a base formulation at 75° C. for 10-20 min, and then cooling to room temperature. The structured oil was prepared by addition of the structurant to the sunflower seed oil, heating the mixture to a temperature above the melting point of the structurant and mixing until uniform. The molten structured oil was then combined with (i.e. added to) the molten surfactant base formulation, which was maintained at the same temperature as the structured oil. After mixing for 10-20 min, the formulation was poured into a mold and cooled to room temperature. The structurant must be, and was, added to the oil phase prior to dispersion of the structured oil phase into the molten surfactant base formulation.

Comparative F was similarly prepared by mixing 20% w/w of sunflower seed oil into a base formulation at 75° C. for 10-20 min followed by cooling to room temperature. The composition of Example 13 of the invention and Comparative F are set forth below.

TABLE 7

Composition of Example 13 and Comparative F

| Component | Example 13 % wt | Comparative B % wt |
|---|---|---|
| Sodium cocoyl isethionate | 20.0 | 20.0 |
| Cocoamidopropyl betaine | 5.0 | 5.0 |
| Sunflower seed oil | 15 | 20.0 |
| Palmitic/Stearic acid | 16.0 | 16.4 |
| Sodium Stearate | 8.0 | 8.2 |
| Glycerol | 10.0 | 10.0 |
| Propylene Glycol | 5.0 | 5.0 |
| Stearine 07 | 5 | 0 |
| 82/18 tallow/coco soap | 2.8 | 2.8 |
| Water | 6.0 | 6.0 |
| Sodium isethionate | 1.9 | 1.9 |
| Coconut fatty acid | 1.2 | 1.2 |
| Sodium chloride | 0.7 | 0.7 |
| Titanium dioxide | 0.8 | 0.8 |
| Fragrance | 1.0 | 1.0 |
| EDTA | 0.02 | 0.02 |
| EHDP | 0.02 | 0.02 |

The benefits of structuring the sunflower seed oil with Stearine 07 are set forth in Table 8 below. The Stearine 07 provided an increase in bar hardness, a significant reduction in the bar rate of wear, and maintained a similar lather volume compared to the bar composition of Comparative F.

TABLE 8

Properties of bar formulation wherein benefit agent oil is structured with Stearine 07 hydrogenated oil.

| | Bar Hardness (mm) | Rate of wear (gm/wash) | Lather (DMV method) |
|---|---|---|---|
| Example 13 | 9 | 2.2 | 26.4 |
| Comparative F | 11 | 3.6 | 28.0 |

Example 14

Benefit agent oil structured with hydrogenated oil in a bar produced via an extrusion process.

The cleansing bar formulation, Example 14, was produced via an extrusion process. Stearine 07 was mixed with sunflower seed oil (48% w/w stearine+52% w/w sunflower seed oil) at a temperature above the melting point of the structurant for 10 min and then the mixture was allowed to cool to room temperature. This provided a material having a yield stress that is on the same order as that of the bar base formulation (i.e. mix of surfactants and bar structuring aids) into which it is to be incorporated. The structured oil can be added to the base formulation at one of several points in the extrusion process. In Example 14, the structured oil was added by mixing with the base at a temperature of about 75° C. in a Patterson mixer until completely dispersed. The compositions were then passed over a chill roll set at 15° C. The flakes from the chill roll were then extruded through a Weber Seelander laboratory scale plodder. Bars were stamped on a Sigma Engineering air-driven press.

Bars were produced at high throughput rates and with good hardness and lathering properties. The bars provided effective deposition of sunflower seed oil.

TABLE 9

Composition of Example 14

| Component | Example 14 - % wt |
|---|---|
| Sodium cocoyl isethionate | 20.0 |
| Cocoamidopropyl betaine | 4.0 |
| Sunflower seed oil | 10.4 |
| Palmitic-stearic acid | 18.8 |
| Sodium stearate | 11.4 |
| Sodium Isethionate | 4.0 |
| Coconut Fatty Acid | 1.3 |
| Stearine 07 | 9.6 |
| PEG 8000 | 11.8 |
| PEG 1450 | 2.1 |
| PEG 200 | 1.4 |
| Sodium Chloride | 0.8 |
| Perfume | 1.0 |
| Titanium Dioxide | 0.12 |
| EHDP | 0.02 |
| EDTA | 0.02 |
| Water | 4.0 |

Examples 15-22

Structuring of a benefit agent oil with a hydrogenated oil for improved bar properties in the presence of a cationic polymer.

The cleansing bar formulations, Examples 15-22, were produced via a melt-cast process. They were prepared by mixing 20% w/w of a structured oil (comprising 3% w/w of the Stearine 07 structurant and 17% w/w sunflower seed oil) into a base formulation at 75° C. for 10 min, adding the cationic polymer (Merquat 100), and then cooling to room temperature. Examples 15-18 are similar formulations with the exception being the level of Merquat 100. Examples 19-22 also are similar to each other except for the Merquat 100 levels. The structured oil was prepared by addition of the structurant to the sunflower seed oil, heating the mixture to a temperature above the melting point of the structurant and mixing until uniform. The molten structured oil was only then combined with (i.e. added to) the molten surfactant base formulation, when both were at a temperature of about 75° C.

TABLE 10

Compositions of Examples 15-22

| Component | Ex. 15 % wt | Ex. 16 % wt | Ex. 17 % wt | Ex. 18 % wt | Ex. 19 % wt | Ex. 20 % wt | Ex. 21 % wt | Ex. 22 % wt |
|---|---|---|---|---|---|---|---|---|
| Sodium cocoyl isethionate | 20.0 | 20.0 | 20.0 | 20.0 | 20.0 | 20.0 | 20.0 | 20.0 |
| Cocoamidopropyl betaine | 5.0 | 5.0 | 5.0 | 5.0 | 5.0 | 5.0 | 5.0 | 5.0 |
| Sunflower seed oil | 17 | 17 | 17 | 17 | 17 | 17 | 17 | 17 |
| Palmitic-Stearic acid | 16.4 | 16.4 | 16.4 | 16.4 | 10.0 | 10.0 | 10.0 | 10.0 |

TABLE 10-continued

Compositions of Examples 15-22

| Component | Ex. 15 % wt | Ex. 16 % wt | Ex. 17 % wt | Ex. 18 % wt | Ex. 19 % wt | Ex. 20 % wt | Ex. 21 % wt | Ex. 22 % wt |
|---|---|---|---|---|---|---|---|---|
| Sodium Stearate | 8.2 | 8.2 | 8.2 | 8.2 | 5.0 | 5.0 | 5.0 | 5.0 |
| Propylene Glycol | 5.0 | 5.0 | 5.0 | 5.0 | 5.0 | 5.0 | 5.0 | 5.0 |
| Glycerine | 10 | 10 | 10 | 10 | 10 | 10 | 10 | 10 |
| Stearine 07 | 3.0 | 3.0 | 3.0 | 3.0 | 3.0 | 3.0 | 3.0 | 3.0 |
| 82/18 tallow/coco soap | 2.8 | 2.8 | 2.8 | 2.8 | 2.8 | 2.8 | 2.8 | 2.8 |
| Water | 6.0 | 6.0 | 6.0 | 6.0 | 6.0 | 6.0 | 6.0 | 6.0 |
| Sodium isethionate | 1.9 | 1.9 | 1.9 | 1.9 | 1.9 | 1.9 | 1.9 | 1.9 |
| Coconut fatty acid | 1.2 | 1.2 | 1.2 | 1.2 | 1.2 | 1.2 | 1.2 | 1.2 |
| Sodium chloride | 0.7 | 0.7 | 0.7 | 0.7 | 0.7 | 0.7 | 0.7 | 0.7 |
| Titanium dioxide | 0.8 | 0.8 | 0.8 | 0.8 | 0.8 | 0.8 | 0.8 | 0.8 |
| PEG 8000 | 0 | 0 | 0 | 0 | 10 | 10 | 10 | 10 |
| Fragrance | 1.0 | 1.0 | 1.0 | 1.0 | 1.0 | 1.0 | 1.0 | 1.0 |
| EDTA | 0.02 | 0.02 | 0.02 | 0.02 | 0.02 | 0.02 | 0.02 | 0.02 |
| EHDP | 0.02 | 0.02 | 0.02 | 0.02 | 0.02 | 0.02 | 0.02 | 0.02 |
| Merquat 100 | 0.25 | 0.5 | 1.0 | 1.5 | 0.25 | 0.5 | 1.0 | 1.5 |

The benefits of incorporating the cationic polymer are to provide a range of sensory attributes.

The invention claimed is:

1. Personal product liquid cleaners composition comprising:
   (1) 1% to 99% by wt. of a surfactant material selected from the group consisting of anionic, nonionic, amphoteric, cationic surfactants and mixtures thereof; and
   (2) 0.1 to 90% by wt. of a structured benefit agent vehicle composition consisting essentially of:
      (a) 50 to 99.9% by wt. of structured benefit agent composition of one or more hydrophobic benefit agents wherein said benefit agents are selected from the group consisting of silicone oils, fats and oils, waxes, hydrophobic plant extracts, hydrocarbons, higher fatty acids, higher alcohols, esters, essential oils, lipids, vitamins, sunscreens, phospholipids particles, anti-aging agents, wrinkle-reducing agents, skin whitening agents, anti-acne agents, sebum reduction agents, fragrance molecules, and mixtures thereof; and
      (b) 0.1 to 50% by wt. of structured benefit agent of a structuring material selected from the group consisting of crystalline structurant selected from the group consisting of hydrogenated oils and fats;
   wherein the crystal in said structuring material has an aspect ratio defined by A/B>1, the length A being understood as the longer of the two dimensions when considering length and width, B;
   wherein, said structured benefit agent is separately formed by adding the structuring material (b) to the benefit agent (a), heating the mixture of (a) and (b) to a temperature above the melting point of (b) to form a molten solution prior to cooling or to combining said molten solution with the said surfactant material; and the structured benefit agent is only then separately combined with the aqueous surfactant phase of said surfactant containing carrying composition in which the structured benefit agent will be used to deliver benefit agent to a substrate; wherein there is provided at least a 5% increase in deposition of benefit agent to said substrate relative to deposition of the same benefit agent not structured, or not being in the presence of a structured benefit agent in the final composition;
   wherein said separately formed structured benefit agent(s) is molten, semi-molten or solid at the time of combination with the carrying composition;
   wherein the structured benefit agent provides deposition of benefit agent greater than 5 µg/cm².

2. A composition according to claim 1, wherein said benefit agent is sunflower seed oil.

3. A composition according to claim 1, wherein structured benefit agent, at time of adding to carrying composition has viscosity no higher than about 250 Pa-s.

4. A composition according to claim 1, wherein said benefit agent is in the form of a droplet and said droplet has a weight average diameter less than 500 µm.

5. A composition according to claim 1 comprising 1 to 75% surfactant.

6. A method of enhancing deposition of hydrophobic benefit agent comprising and providing smooth skin feel which method comprises applying a personal product liquid cleanser composition comprising:
   (1) 1% to 99% surfactant material selected from the group consisting of anionic, nonionic, amphoteric, cationic surfactants and mixtures thereof; and
   (2) 0.1 to 90% of a benefit agent vehicle composition consisting essentially of:
      (a) 50 to 99.9% by wt. of structured benefit agent composition of one or more hydrophobic benefit agents wherein agent is selected from the group consisting of silicone oils, fats and oils, waxes, hydrophobic plant extracts, hydrocarbons, higher fatty acids, higher alcohols, esters, essential oils, lipids, vitamins, sunscreens, phospholipids particles, anti-aging agents, wrinkle-reducing agents, skin whitening agents, anti-acne agents, sebum reduction agents, fragrance molecules, and mixtures thereof; and
      (b) 0.1 to 50% by wt. of structured benefit agent of a structuring material selected from the group consisting of crystalline structurant selected from the group consisting of hydrogenated oils and fats;
   wherein the crystal in said structuring material has an aspect ratio defined by A/B>1, length A being understood as the longer of the two dimensions when considering length and width, B;
   wherein, said structured benefit agent is separately formed by adding the structuring material (b) to the benefit agent (a), heating the mixture of (a) and (b) to a temperature above the melting point of (b) to form a molten solution prior to cooling or to combining said molten solution with the said surfactant material; and the structured benefit agent is only then separately combined with the aqueous surfactant phase of said surfactant containing carrying composition in which the structured benefit agent will be used to deliver benefit agent to a substrate;

wherein there is provided at least a 5% increase in deposition of benefit agent to said substrate relative to deposition of the same benefit agent not structured, or not being in the presence of a structured benefit agent in the final composition wherein said separately formed structured benefit agent(s) is molten, semi-molten or solid at the time of combination with the carrying composition;

wherein the structured benefit agent provides deposition of benefit agent greater than 5 $\mu g/cm^2$.

* * * * *